(12) United States Patent
Oury et al.

(10) Patent No.: US 8,709,479 B2
(45) Date of Patent: Apr. 29, 2014

(54) SUBLINGUAL COATED TABLET OF FENTANYL

(75) Inventors: Pascal Oury, Le Chesnay (FR); Guillaume Benoist, Chartres (FR); Catherine Herry, Saint Pierre les Elbeuf (FR); Joseph Duvochel, Mérindol (FR)

(73) Assignee: Ethypharm (FR)

( * ) Notice: Subject to any disclaimer, the term of this patent is extended or adjusted under 35 U.S.C. 154(b) by 1370 days.

(21) Appl. No.: 11/384,763

(22) Filed: Mar. 20, 2006

(65) Prior Publication Data

US 2006/0210632 A1 Sep. 21, 2006

(30) Foreign Application Priority Data

Mar. 18, 2005 (FR) ...................................... 05 02727

(51) Int. Cl.
  *A61K 9/24* (2006.01)

(52) U.S. Cl.
  USPC .......................................... 424/472; 514/317

(58) Field of Classification Search
  None
  See application file for complete search history.

(56) References Cited

U.S. PATENT DOCUMENTS

| | | | |
|---|---|---|---|
| 3,141,792 A * | 7/1964 | Lachman et al. ............. | 118/697 |
| 4,671,953 A | 6/1987 | Stanley et al. | |
| 4,828,840 A | 5/1989 | Sakamoto et al. | |
| 5,061,493 A | 10/1991 | Ayache et al. | |
| 5,202,128 A | 4/1993 | Morella et al. | |
| 5,411,745 A | 5/1995 | Oshlack et al. | |
| 6,077,544 A | 6/2000 | Debregeas et al. | |
| 6,200,604 B1 * | 3/2001 | Pather et al. ................... | 424/466 |
| 6,248,363 B1 | 6/2001 | Patel et al. | |
| 6,248,760 B1 | 6/2001 | Wilhelmsen | |
| 6,770,298 B1 | 8/2004 | Debregeas et al. | |
| 2001/0016593 A1 | 8/2001 | Wilhelmsen | |
| 2002/0028246 A1 | 3/2002 | Debregeas et al. | |
| 2003/0191147 A1 | 10/2003 | Sherman et al. | |
| 2004/0247677 A1 | 12/2004 | Oury et al. | |
| 2006/0210632 A1 | 9/2006 | Oury et al. | |
| 2006/0216352 A1 * | 9/2006 | Nystrom et al. ............... | 424/489 |
| 2007/0003620 A1 | 1/2007 | Marechal et al. | |

FOREIGN PATENT DOCUMENTS

| | | | |
|---|---|---|---|
| EP | 0553392 A1 | 4/1993 | |
| EP | 0803250 | 10/1997 | |
| EP | 1103252 A1 | 5/2001 | |
| EP | 1627631 A2 | 2/2006 | |
| FR | 2771291 A1 | 5/1999 | |
| JP | 2004269545 A | 9/2004 | |
| NZ | 516726 | 6/2004 | |
| RU | 2125445 C1 | 1/1999 | |
| RU | 2144353 C1 | 1/2000 | |
| RU | 2209628 C2 | 8/2003 | |
| WO | 9103236 A1 | 3/1991 | |
| WO | 9405263 A1 | 3/1994 | |
| WO | 94/09762 * | 5/1994 | ............... A61K 9/64 |
| WO | WO 94/09762 * | 5/1994 | ............... A61K 9/64 |
| WO | WO 94/09762 * | 11/1994 | |
| WO | 9531972 A1 | 11/1995 | |
| WO | 9618389 A1 | 6/1996 | |
| WO | 9940918 A1 | 8/1999 | |
| WO | 0016751 A1 | 3/2000 | |
| WO | WO 00/16750 | 3/2000 | |
| WO | 0057858 A1 | 10/2000 | |
| WO | WO 00/57858 | 10/2000 | |
| WO | 0106982 A2 | 2/2001 | |
| WO | WO 03002099 | 1/2003 | |
| WO | 03013479 A1 | 2/2003 | |

OTHER PUBLICATIONS

Shelukar et al "Identification and characterization of factors controlling tablet coating uniformity in a Wurster coating process," Powder Technology 110 (2000) 29-36.*
Abstract of Zhang et al., "Oral mucosal drug delivery: clinical pharmacokinetics and therapeutic applications", Clin. Pharmacokinet, 2002; 41(9):661-80.
International Search Report for PCT/EP2006/003304, Jul. 12, 2006.
U.S. Appl. No. 11/909,057, filed on Sep. 18, 2007.
Merck Index, Thirteenth Edition, 2001, Merck & Co., Inc. Whitehouse Station, NJ, pp. 275, 279, and 1016.
Pather et al., Enhanced Buccal Delivery of Fentanyl Using the Ora Vescent Drug Delivery System, Drug Delivery Technology, vol. 1, No. 1, Oct. 2001, pp. 1-6.
Morissette et al., High-throughput crystallization: polymorphs, salts, co-crystals and solvates of pharmaceutical solids, Advanced Drug Delivery Reviews, vol. 56, 2004, pp. 275-300.
Bredenberg et al., In vitro and in vivo evaluation of a new sublingual tablet system for rapid oromucosal absorption using fentanyl citrate as the active substance, European Journal of Pharmaceutical Sciences, vol. 20, 2003, pp. 327-334.
Ishikawa et al., Preparation of Rapidly Disintegrating Tablet Using New Types of Microcrystalline Cellulose (PH-M Series) and Low Substituted-Hydroxypropylcellulose or Spherical Sugar Granules by Direct Compression Method, Chem. Pharm. Bull, 2001, vol. 49, No. 2, pp. 134-139.
Vippagunta et al., Crystalline solids, Advanced Drug Delivery Reviews, vol. 48, 2001, pp. 3-26.

* cited by examiner

*Primary Examiner* — Suzanne Ziska
(74) *Attorney, Agent, or Firm* — Caesar, Rivise, Bernstein, Cohen & Pokotilow, Ltd.

(57) ABSTRACT

The present invention relates to a fentanyl coated tablet and to the method for the preparation thereof.

23 Claims, 1 Drawing Sheet

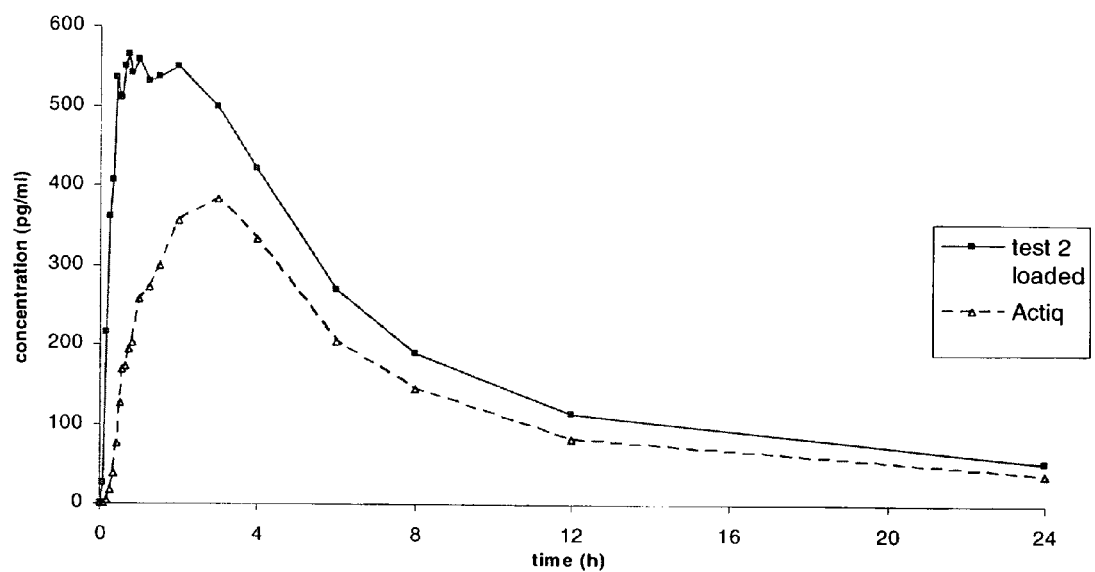

SUBLINGUAL COATED TABLET OF FENTANYL

The subject of the present invention relates to a sublingual coated tablet consisting of a compressed core devoid of pharmaceutically active substance and comprising one or more diluting agents, and a coating comprising at least fentanyl as active substance, and also to a method for preparing such a sublingual coated tablet.

In the present invention, "fentanyl as active substance", is intended to mean, fentanyl and derivatives thereof, in the base form as well as in the form of their pharmaceutically acceptable salts, in any polymorphic form, in racemic or enantiomeric form.

Derivatives of fentanyl comprise alfentanil, sufentanil and remifentanil.

The term "pharmaceutically acceptable salts" is intended to mean the derivatives of the compounds described in which the pharmaceutically active base compound is converted to its salt with a base or acid, examples of pharmaceutically active salts comprising in particular organic and inorganic acid salts of basic residues, such as amines, alkali metal derivatives or organic salts of acidic residues, such as carboxylic acids, and the like.

Examples of pharmaceutically acceptable salts of fentanyl comprise fentanyl citrate and fentanyl hydrochloride. Examples of derivatives of fentanyl and their pharmaceutically acceptable salts comprise alfentanyl, alfentanyl hydrochloride, sufentanyl, sufentanyl citrate, remifentanyl, remifentanyl hydrochloride.

BACKGROUND OF THE INVENTION

Sublingual administration has an advantage for active substances which, when given orally, are subject to a substantial effect of first passage through the liver, resulting in rapid metabolization and a loss of therapeutic activity related to the activity of the liver enzymes that convert the molecule into inactive metabolites, or the activity of which is decreased because of this bioconversion.

In the case of sublingual administration, systemic passage is very rapid due to the considerable permeability and vascularization of the buccal mucosa. This makes it possible to obtain an effect which is more rapid than that obtained with oral administration. In the case of oral administration, in fact, the tablet is swallowed and systemic passage occurs only at the level of the gastrointestinal mucosa, i.e. later.

Moreover, sublingual administration can also allow the administration of active substances which are not normally absorbed at the level of the stomach mucosa or digestive mucosa after oral administration, or alternatively which are partially or completely degraded in acidic medium after ingestion of the tablet.

Fentanyl citrate is presently available in the form of a candy-on-a-handle (lollipop) for transmucosal administration which is marketed under the trade name Actiq®. The problem linked to this specific form is that the patient must keep the lollipop in the mouth for at least 15 minutes in order to obtain the desired amount of fentanyl. Furthermore, the amount of absorbed fentanyl is dependent of the frequency of saliva swallowing and thus very dependent of the patient. It is thus difficult to precisely check the absorbed amount of fentanyl.

For this reason, it is thought that formulation of fentanyl in the form of sublingual tablets would be better.

The sublingual tablets known from the prior art are usually prepared by direct compression of a mixture of powders comprising the active substance and compression excipients, such as diluents, binders, disintegrating agents and adjuvants.

In an alternative method of preparation, the active substance and the compression excipients can be dry- or wet-granulated beforehand.

In this case, the active substance is distributed throughout the mass of the tablet.

WO 00/16750 describes a tablet for sublingual use that disintegrates rapidly and comprises an ordered mixture in which the active substance is in the form of microparticles which adhere to the surface of water-soluble particles that are substantially greater in size, constituting a support for the active microparticles, the composition also comprising a mucoadhesive.

WO 00/57858 describes a tablet for sublingual use, comprising an active substance combined with an effervescent system intended to promote absorption, and also a pH modifier.

Sublingual administration is an administration route which has certain limits due to the size of the sublingual cavity in which the tablet is placed, to the limited volume of saliva for solubilizing the active substance or else to the limited amount of active substance that can cross the buccal mucosa.

Because of these limits, tablets in which the active substance is distributed uniformly within the mass of the tablet have certain drawbacks that the present invention aims to solve.

A first drawback of these tablets in which the active substance is dispersed within the mass is the dependency which exists between the size of the tablet and the dosage of the active substance. Thus, if it is intended to provide tablets of various dosages, it will be necessary to have tablets of various sizes.

It may therefore be that the size of the tablet containing the highest dose, in particular its diameter, is no longer suitable for sublingual administration.

This may force those skilled in the art to modify the formula of the tablet containing the highest dose, in particular so as to adapt its size to sublingual use, which means, in the end, having tablets with different qualitative and/or quantitative formulae for one and the same active substance, which is neither economically desirable, nor desirable in terms of safety.

Moreover, sublingual administration requires the use of an active substance of specific particle size, usually consisting of a population for which the diameter is less than 10 µm, preferably less than 5 µm, as measured by the usual techniques, for example by laser diffraction.

This choice is aimed at ensuring rapid and complete solubilization of said active substance in the saliva and allowing immediate and sufficient systemic passage so as to obtain an instantaneous effect.

Now, the use of particles of this size in tablets means that it is also necessary to adapt the particle size of the excipients constituting the mass of the tablet and to very precisely define the mixing parameters for the pulverulent mass, in order to obtain an ordered mixture in which the active substance is uniformly distributed, without witnessing the appearance of a segregation phenomenon in the feed hopper of the tablet press, which would be liable to compromise the uniformity of content of the tablets during the compression.

The risk of appearance of a segregation phenomenon is further increased when the unit dose of active substance in each tablet is low. This is, for example, the case with fentanyl, for which the unit dose is generally less than a milligram to a few milligrams.

It is then difficult to obtain an acceptable uniformity of content for the same batch throughout the compression step, the active substance then being highly diluted in the pulverulent mixture of excipients.

For tablets for sublingual administration in which the active substance is uniformly dispersed in the mass, the release of the active substance is also dependent upon the rate of disintegration of the tablet.

The prior art describes tablets that disintegrate rapidly, suitable for sublingual administration, in which the active substance is distributed within the mass of the tablet.

It is known that these tablets usually have a low hardness, often less than 40 N, and exhibit a tablet friability that is too great, so that they must be handled with care.

In the case of a tablet having a greater hardness, the disintegration is less rapid, so that the tablet erodes gradually while releasing the active substance from the surface of the tablet to its centre.

It is therefore particularly advantageous to have a formulation for sublingual administration that can rapidly release the active substance and allow immediate absorption thereof, without this release being dependent upon the rate of disintegration or upon the hardness of the tablet.

When the tablet is intended to disintegrate rapidly and without chewing, the disintegration leads to the formation of a pulp or of a suspension that can be unintentionally swallowed.

The viscosity of the pulp or suspension, which is related to the use of disintegrating agents or of swelling agents intended to accelerate the disintegration, can cause a swallowing reflex.

Consequently, part of the active substance is swallowed before being absorbed by the buccal mucosa.

The absorption at the level of the buccal mucosa, on which the bioavailability of the active substance directly depends, is therefore dependent upon the nature of the excipients used in this type of rapid disintegration formulation.

The Applicant has now demonstrated that, unexpectedly and surprisingly, it is possible to remedy these drawbacks by means of a solid unit form, in particular a coated tablet.

SUMMARY OF THE INVENTION

The coated tablet according to the invention consists of a compressed core devoid of pharmaceutically active substance and comprising one or more diluting agents, and a coating comprising at least fentanyl as active substance.

This form is particularly suitable for sublingual administration, since it contains the active substance, not in the mass of the tablet as in the prior art, but at the surface of the compressed core.

The release of the pharmaceutically active substance is thus rendered completely independent of the rate of disintegration or of the hardness of the tablet, if the compressed core is formulated such that it only disintegrates after the complete release of the pharmaceutically active substance.

Once the layer forming the coating and comprising the pharmaceutically active substance is completely solubilized in the fluids of the buccal cavity, in particular in the saliva, the compressed core can be swallowed or else can be kept under the tongue until complete disintegration thereof, the resulting suspension being formed and swallowed only after absorption of the active substance.

Moreover, the composition of the invention is perfectly suitable for the preparation of low-dose tablets, since the application of the coating by spraying has the advantage of a uniform distribution around the compressed core, and thus limits any risk of heterogeneity of content in the same batch of tablets, avoiding any possible demixing linked to the preparation of a mixture of powders in which the pharmaceutically active substance is diluted.

The present invention also solves the problem of the size of the tablet when the dosage range is spread by a considerable factor between the lowest unit dosage and the highest.

In fact, the size of the tablet no longer depends on the dosage of the pharmaceutically active substance in the tablet, but can be chosen independently by selecting the size of the compressed core onto which the layer forming the coating comprising the pharmaceutically active substance is sprayed.

By virtue of the present invention, it is possible to prepare a compressed core of single size for the entire dosage range for the same pharmaceutically active substance.

It is then the thickness of the coating comprising the active substance that regulates the final dosage of the tablet.

This characteristic is particularly advantageous in the case of buccal or sublingual administration, for which the size of the tablet is adjusted so as to be readily placed in the buccal cavity, whatever its dosage of pharmaceutically active substance.

This form also makes it possible to have a simple means of distinguishing the dosages by introducing in particular into the coating comprising the pharmaceutically active substance a different dyestuff according to the final dosage of the tablet. It can also be envisaged to colour the compressed core, for example when the coating is translucent.

BRIEF DESCRIPTION OF THE DRAWINGS

FIG. 1. A Crossover Single-Dose Comparative Bioavailability Study of Tablets prepared according to example 2 versus Actiq® 0.4 mg in Healthy Male Volunteers under Fasting Conditions. Tablets prepared according to example 2 and the reference product which were each administered to 10 patients and the Cmax, Tmax and AUC were measured. Both the invention and the reference product contain fentanyl citrate in an amount equivalent to 0.4 mg of fentanyl base. Blood sampling points: before dosing and at the following times thereafter in each period: 5, 10, 15, 20, 25, 30, 35, 40, 45, 50, 60, 75, 90 minutes and at 2, 3, 4, 6, 8, 12 and 24 hours post-dose

DETAILED DESCRIPTION

The compressed core, devoid of pharmaceutically active substance, comprises at least one diluting agent.

The compressed core can in particular comprise, in addition to the diluting agent(s), one or more excipients chosen from binders, swelling agents, disintegrating agents, lubricants, antistatic agents and adjuvants, or mixtures thereof.

The diluting agent is chosen from the group comprising in particular cellulose derivatives, and preferably microcrystalline cellulose, polyols, starches alone, and sugar derivatives.

The diluting agent can advantageously be chosen from sucrose, lactose, fructose, dextrose, mannitol, sorbitol, lactitol, erythritol, xylitol, dicalcium phosphate, tricalcium phosphate or a microcrystalline cellulose, alone or as a mixture.

The diluting agents preferably used are those that exist in a directly compressible form, the particle size of which is greater than 100 µm.

In a first embodiment, the compressed core comprises a mixture of diluting agent formed from mannitol and microcrystalline cellulose.

In a specific embodiment of the invention, the diluting agent can consist of an inert support, also called "neutral microgranule", "neutral substance" or "sugar sphere", the shape of which is substantially spherical and the particle size distribution of which, measured by known methods such as laser diffraction, shows a monomodal profile such that the variation relative to the ranges indicated in the Pharmacopoeiae, for example the American Pharmacopoeia (USP XVII, 1990), is low, such that the diameter of the neutral microgranules is substantially uniform.

These morphology and size characteristics confer on the neutral microgranules excellent properties of flow in the feed hoppers of the tablet presses and good compressibility, which makes it possible to prepare compressed cores by direct compression of these neutral microgranules without the addition of other excipients with the exception of a lubricant, and at a rapid rate.

These characteristics thus make it possible to produce large volumes in a minimum amount of time and make the method for preparing these compressed cores particularly simple and economical.

The inert supports are usually prepared by coating of crystalline sucrose with a suspension of starch in sugar syrup, such as those sold by the company NP Pharm under the trademark Suglets® or NPTAB®.

These commercially available inert supports have a diameter usually of between 180 and 1400 µm, and have the advantage of being sold in the form of a size selection.

The inert supports that are preferred in the context of the present invention have a diameter of between 180 µm and 500 µm, and even more preferably of between 180 and 250 µm.

The diluting agent is present in proportions that can range up to 100% by mass of the compressed core, preferably of between 50% and 95% by mass relative to the mass of the excipient core.

The binder is used in dry form and can be a starch, a sugar, polyvinylpyrrolidone or carboxymethylcellulose, alone or as a mixture.

The binder is used in a proportion that can range up to 15% by mass, preferably less than 10% by mass, calculated relative to the mass of the compressed core.

The swelling agent is chosen from the group comprising microcrystalline cellulose, starches, modified starches, such as carboxymethyl starch or sodium starch glycolate, alginic acid or sodium alginate, and mixtures thereof.

The swelling agent is used in a proportion that can range up to 20%, preferably of between 1 and 15% by mass, calculated relative to the mass of the compressed core.

The disintegrating agent can be chosen from the group comprising in particular crosslinked sodium carboxymethylcellulose referred to by the term croscarmellose, crosslinked polyvinylpyrrolidones referred to by the term crospovidone, and mixtures thereof.

The disintegrating agent is used in a proportion that can range up to 20%, preferably of between 1 and 20% by mass, and even more preferably of between 5 and 15% by mass, calculated relative to the mass of the compressed core.

The lubricant is chosen from the group comprising magnesium stearate, stearic acid, sodium stearyl fumarate, polyoxyethylene glycols, sodium benzoate, a pharmaceutically acceptable oil, preferably dimethicone or liquid paraffin, or mixtures thereof.

The lubricant is used in a proportion that can range up to 2%, preferably of between 0.02 and 2% by mass, even more preferably of between 0.5 and 1% by mass, calculated relative to the mass of the compressed core.

The antistatic agent can be chosen from the group comprising micronized or nonmicronized talc, colloidal silica (Aerosil® 200), treated silica (Aerosil® R972) or precipitated silica (Syloid® FP244), and mixtures thereof.

The antistatic agent is used in a proportion that can range up to 5% by mass, calculated relative to the mass of the compressed core.

Adjuvants, for example dyes, sweeteners and/or flavourings, can also be added to the mixture intended to be compressed.

These adjuvants are identical to those described below in relation to the coating of the tablet according to the invention.

The active substance can be in the form of a powder or of microcrystals.

If the active substance is completely or partly in suspension in the sprayed solution, the powder or the microcrystals have a size of between 0.5 µm and 10 µm, preferably of between 4 µm and 6 µm.

In this manner, when the coated tablet of the invention is directly administered sublingually, only the active substance passes into the general circulation and exerts its action, the antagonist, for its part, not being absorbed.

The pharmaceutically acceptable excipients optionally present are chosen from binders, soluble agents, surfactants, absorption promoters, bioadhesive agents, antistatic agents, pH modifiers, acid/base pairs that produce an effervescence, sweeteners, flavourings, dyes, and mixtures thereof.

The binder, which is optionally present in the coating, is used in proportions that can range up to 95% by mass relative to the dry mass of the coating, preferably up to 30% by mass relative to the dry mass of the active layer.

Its role is to bind the active substance to the compressed core without loss of material, or to "bond" the powder or the microcrystals of active substance and the other excipients, in order to give a homogeneous layer of active substance, evenly distributed around the compressed core.

The binder can be chosen from cellulose-based polymers, acrylic polymers, polyvinylpyrrolidones, such as povidones and copovidones, polyvinyl alcohols, alginic acid, sodium alginate, starch, pregelatinized starch, sucroses and derivatives thereof, guar gum and polyethylene glycols, and mixtures thereof.

The binder is preferably chosen from polymers that are hydrophilic and/or soluble at the pH of saliva, so as to allow a more rapid release of the active substance, such as polyvinylpyrrolidones and cellulose-based polymers, acrylic polymers and polyethylene glycols.

The polyvinylpyrrolidone can be chosen from polymers having a molecular mass of between 10 000 and 50 000.

The cellulose-based polymer is chosen from hydroxylated derivatives, for example hydroxypropylmethylcellulose, hydroxypropylcellulose, hydroxymethylcellulose, hydroxypropylmethylcellulose phthalate and hydroxypropylmethylcellulose acetosuccinate.

The preferred hydroxypropylmethylcellulose is chosen from those for which the apparent viscosity (aqueous solution at 2% m/m, at 20° C., USP method) is between 2.4 and 18 cP, and even more preferably between 2.4 and 5 cP.

The preferred polyethylene glycol is chosen from those for which the nominal molecular mass is 4000 or 6000 g/mol.

The soluble agent, which may be optionally present in the coating, is used in a proportion that can range up to 90% by mass, preferably of between 1% and 60%, and even more preferably of between 30 and 60% by mass, calculated relative to the dry mass of the coating applied around the compressed core.

This soluble agent is used in particular for improving the solubilization of the active substance by accelerating the solubilization of the coating comprising the active substance.

The soluble agent can be chosen from the group of sugars such as sucrose, lactose or dextrose, of polyols such as mannitol, sorbitol or lactitol, or else of inorganic salts such as sodium chloride.

The surfactant, which is optionally present in the coating, can be chosen from cationic, anionic, nonionic or amphoteric agents, alone or as a mixture.

The surfactant can be chosen, for example, from compounds such as sodium lauryl sulphate, the monooleate, the monolaurate, the monopalmitate, the monostearate, the trioleate, the tristearate or any other ester of polyoxyethylenated sorbitan, preferably Tween® 20, 40, 60 or 80, glycerides of polyoxyethylenated fatty acids, these fatty acids being saturated or unsaturated and composed of at least 8 carbon atoms, poloxamers, such as poloxamer 188, ethylene oxide/propylene oxide block copolymers, such as Pluronic® F68 or F87, lecithin, stearyl alcohol, cetearyl alcohol, cholesterol, polyoxyethylenated castor oil, fatty alcohol polyoxyethylenated ethers, such as the Brij® products, and polyoxyethylenated stearates.

The surfactant is advantageously present in a proportion that can range up to 20%, preferably of between 0.1 and 20% by mass relative to the total dry mass of the coating.

The absorption promoters, which are optionally present in the coating, are compounds that make it possible to improve the absorption of the active substance through the walls of the buccal cavity to the bloodstream.

These compounds can be chosen from the group comprising, for example, sodium lauryl sulphate, sodium caprate or chitosans, and also P-glycoprotein (P-gp) inhibitors, such as polysorbate 80, Cremophor® EL (hydrogenated castor oil) or Solutol® HS-15 (PEG-HS or polyethylene glycol-660 12-hydroxystearate).

The bioadhesive agents can be chosen from the group comprising, for example, carbomers, sodium carboxymethylcellulose, sodium alginate, hydroxypropylmethylcellulose, hydroxypropylcellulose, hydroxyethylcellulose, ethylcellulose, gelatine, guar gum, polyethylene oxide)s (trade name Polyox®) and dextran.

The antistatic agent, which is optionally present in the coating, can be chosen from the same group of compounds as the antistatic agent of the compressed core. It can be identical to or different from the latter.

The antistatic agent is used in a proportion that can range up to 60% by mass, calculated relative to the dry mass of the coating applied around the compressed core.

The pH modifier is chosen from the group comprising citric acid and sodium citrate or potassium citrate, sodium hydroxide, monoethanolamine, diethanolamine, sodium bicarbonate or potassium bicarbonate, sodium phosphate, tartaric acid, propionic acid, lactic acid, malic acid and monosodium glutamate.

The acid/base pair that produces an effervescence is formed from an alkaline agent and an acidic agent which are chosen from those that are pharmaceutically acceptable, such that, in the presence of water, they allow the release of a gas.

The advantage of using an effervescent mixture in the active layer formed around the compressed core is that of facilitating the rapid dissolution of the active layer formed around the compressed core upon contact with saliva, and thus obtaining, through the release of a pharmaceutically acceptable gas and induction of a buccal micro pH, rapid solubilization of the active substance at the buccal or sublingual mucous membranes and an improved systemic passage while at the same time improving the organoleptic properties so as to decrease the feeling of the active substance in the buccal cavity, or inducing a pleasant slightly acid taste.

The acidic agent is a proton-donating compound which can react with an alkaline agent so as to form a gas which causes the effervescence of the liquid in which this gas is released.

The acidic agent can consist of any inorganic or organic acid, in the form of a free acid, an acid anhydride or an acid salt.

This acid is chosen from the group comprising in particular tartaric acid, citric acid, maleic acid, fumaric acid, malic acid, adipic acid, succinic acid, lactic acid, glycolic acid, alpha-hydroxy acids, ascorbic acid and amino acids, and also the salts and derivatives of these acids.

The alkaline agent consists of a compound capable of generating a gas by reaction with a proton-donating compound. The gas formed is carbon dioxide, oxygen or any other type of biocompatible gas.

The alkaline agent is chosen from the group comprising potassium carbonate, lithium carbonate, sodium carbonate, calcium carbonate, ammonium carbonate, L-lysine carbonate, arginine carbonate, sodium glycine carbonate, sodium carbonates of amino acids, anhydrous sodium perborate, effervescent perborate, sodium perborate monohydrate, sodium percarbonate, sodium dichloroisocyanurate, sodium hypochlorite, calcium hypochlorite, and mixtures thereof.

In the context of the present invention, the term "carbonate" is intended to mean, without distinction, carbonates, sesquicarbonates and hydrogen carbonates.

The respective amounts of acidic agent and of alkaline agent are adjusted such that the reaction between the alkaline agent and the protons released by the acid allows the generation of a sufficient amount of gas to obtain a satisfactory effervescence.

When it is necessary to adjust the pH or to produce an effervescence over a longer period, for example so as to allow the absorption of a higher dose of active substance, a fraction of the pH modifier or of the effervescent pair can be included in the compressed core itself.

Tablets according to the invention containing fentanyl base or a pharmaceutically acceptable salt thereof usually contain from 0.2 to 1.6 mg fentanyl base, e.g. 0.2, 0.4, 0.6, 0.8, 1.0, 1.2 or 1.6 mg. In a preferred embodiment the tablet contains 0.4 mg fentanyl base.

According to a specific embodiment, the tablet according to the invention comprises another coating layer comprising an alkaline compound.

The alkaline coating layer allows the provision of a local alkaline pH when the tablet is placed in the buccal cavity which enhances the absorption of fentanyl by mucosa.

The alkaline coating layer may optionally comprise excipients identical to those present in the fentanyl layer.

The alkaline coating layer may be present above or under the fentanyl layer.

According to another embodiment, the alkaline compound can be present within the fentanyl layer.

The alkaline compound is selected from the group comprising tris, tartrate, acetate, phosphate, and preferably anhydrous disodium phosphate and mixtures thereof.

Advantageously, the fentanyl tablets according to the invention comprise a sweetener and/or flavouring in order to mask the bitterness of fentanyl.

Suitable sweeteners may be selected from the group comprising in particular aspartame, acesulfam potassium, sodium saccharinate, neohesperidine dihydrochalcone, sucralose, monoammonium glycyrrhizinate, and mixtures thereof.

Suitable flavorings and colorants are those commonly used in pharmacy for the preparation of tablets.

The sweeteners and the flavourings of the coating may be chosen from the same group as those used in the compressed core, but it is possible for them not to be the same compound.

The colorant is used in an amount that can range up to 1% by weight, calculated relative to the dry weight of the coating applied around the compressed core.

According to an embodiment of the invention, it is possible to use colouring of the coating and/or the optional alkaline layer as a code to indicate the dosage of fentanyl. In fact, whatever the dosage is, the size of the tablets can be the same. In order to make the difference between different dosages, a specific colour can be associated to a specific dosage.

An advantage of fentanyl tablets according to the invention is the rapid dissolution of the coating, and thus the rapid release of fentanyl, before the disintegration of the core.

Advantageously, in addition to the rapid dissolution as defined above, the coated tablet of the invention has a disintegration time of less than 15 min, preferably of 5 to 15 min.

Fentanyl tablets according to the invention are useful in the management of breakthrough pain, in particular breakthrough cancer pain, by sublingual administration in patients who are tolerant to opioid therapy. Breakthrough pain means a transitory flare of pain of moderate to severe intensity occurring on a background of otherwise controlled pain. Patients considered opioid tolerant are those who are taking at least 60 mg morphine/day, at least 25 µg transdermal fentanyl/hour, at least 30 mg of oxycodone daily, at least 8 mg of oral hydromorphone daily or an equianalgesic dose of another opioid for a week or longer.

The solid pharmaceutical composition of the invention can be prepared by means of a method comprising at least the following steps:
1. compressing a diluting agent or a mixture of excipients comprising at least one diluting agent;
2. spraying a solution or a suspension comprising fentanyl as an active substance and, optionally, at least one pharmaceutically acceptable excipient, onto the compressed core formed in the preceding step; and
3. optionally spraying a solution or suspension comprising an alkaline compound and, optionally, at least one pharmaceutically acceptable excipient, step 3 being carried out before, after or simultaneously with step 2.

The compression of the excipient or the mixture of excipients so as to obtain the compressed core can be carried out on an alternating or rotary tablet press.

The compressing step can optionally be preceded by a step consisting in mixing the excipients intended to be compressed, in particular so as to allow the addition of a lubricant.

When the compressed core is exclusively formed from spherical neutral microgranules, the compression is carried out directly without any prior mixing step other than the addition of a lubricant.

If necessary, the lubricant can be sprayed in the external phase onto the wall of the dies and of the punches of the tablet press so as to facilitate the ejection of the tablet formed.

The stress exerted during the compressing step can range from 5 kN to 50 kN, and are adjusted so as to obtain a tablet having a hardness of preferably between 10 and 180 N, more preferably between 15 and 100 N, measured according to the method of the European Pharmacopoeia (2.9.8).

Preferably, the hardness of the tablet is adjusted so as to obtain a friability, measured according to the method of the European Pharmacopoeia, of less than 1%.

The coated tablets can have a diameter of between 2 and 14 mm and a round, oval, oblong or other shape, can have a flat, convex or other surface, and can optionally have engraving.

Preferably, the coated tablets have a round biconvex shape, which is an advantageous shape for both the coating process and the contact of the coated tablet with saliva when said tablet is placed in the buccal cavity.

As explained above, the size of the compressed cores can be readily adjusted so as to obtain the best compromise according to the various criteria, namely the unit dosage of the active substance, the solubility of the active substance, the ratio of the lowest dosage to the highest dosage and the final size of the tablet.

It is thus possible to modulate the thickness of the coating layer such that the latter will be solubilized as rapidly as possible so as to allow a systemic passage that is immediate and uniform between the various unit dosages and uninfluenced by the rate of disintegration of the tablet itself.

However, although the disintegration time of the tablet does not influence the rate of release of the active substance, it is preferable, for the patient's comfort, for the disintegration time to be less than 15 minutes, preferably less than 10 minutes, and even more preferably less than 5 minutes.

However, in order to prevent the tablet from disintegrating at the same time as the coating layer(s), it is preferable for the disintegration time to be greater than 1 minute, preferably greater than 2 minutes.

The disintegration time is measured in vivo by placing the coated tablet in the sublingual cavity, and measuring, using a stopwatch, the time that elapses between the beginning of the measurement and the moment when the coated tablet has completely disintegrated under the action of saliva and without chewing, so as to form only a viscous pulp, the patient not having to use, during all this time, any action of the jaws.

The spraying of the layer forming the coating is usually carried out in a sugar-coating pan, a perforated drum or in a fluidized bed.

The choice of the equipment makes it possible to control the application of the coating of the compressed cores and to prevent any sticking phenomena, linked to the nature of the active substance and of the excipients of the coating composition, and to the various parameters of the method (temperature, air pressure, for example, solution flow rate).

The layer comprising the active substance forming the coating is distributed uniformly over the surface of the compressed core.

The composition of the coating layer is adjusted such that the latter is completely solubilized when the table disintegrates.

In particular, for water-insoluble substances, it is possible to form a coating layer in which the active substance is in the form of a solid dispersion, obtained by coprecipitation of the active substance with a hydrophilic polymer.

In a preferred embodiment, the spraying of the coating onto the compressed cores is carried out in a perforated drum, in particular in a perforated drum having sections with triangular profiles, parallel to one another and defining the apertures between them, such as that described in patent application EP 1044064.

The sugar-coating pan or the perforated drum makes it possible to maintain the integrity of the compressed cores during the spraying by reducing the impacts between the compressed cores, compared with the fluidized air bed.

The coating composition is sprayed in the form of a solution, a suspension or a colloidal dispersion in an organic or aqueous solvent, or mixtures thereof, and is then dried.

The organic solvent can be chosen from ethanol, isopropanol, tetrahydrofuran, isopropyl ether, acetone, methyl ethyl ketone, methylene chloride or a mixture of these solvents.

Purified water is the solvent preferably used if the coating is devoid of effervescent agents; on the other hand, an organic solvent has to be used when the sprayed composition contains an effervescent acid/base pair.

The spraying of the layer containing an alkaline substance is usually carried out in a sugar-coating pan, a perforated drum or in a fluidized bed.

Said step can be carried out directly onto the compressed cores, or simultaneously with the spraying step of the coating containing fentanyl, or onto the coating layer containing fentanyl.

It is preferred to carry out said step as an over-coating, i.e. onto the coating layer containing fentanyl.

The choice of the equipment makes it possible to control the application of the alkaline coating of the compressed cores and to prevent any sticking phenomena, linked to the nature of the active substance and of the excipients of the alkaline coating composition, and to the various parameters of the method (temperature, air pressure, for example, solution flow rate).

The alkaline is distributed uniformly over the surface of the compressed core or over the coating layer containing fentanyl.

The composition of the alkaline coating layer is adjusted such that the latter is completely solubilized when the tablet comes into contact with the saliva in order to provide for a local alkaline pH around the buccal area where the tablet is placed.

The same device as the one used for carrying the coating of fentanyl can be used to carry out the alkaline coating.

The alkaline coating composition is sprayed in the form of a solution, a suspension or a colloidal dispersion in an organic or aqueous solvent, or mixtures thereof, and is then dried.

The organic solvent can be chosen from ethanol, isopropanol, tetrahydrofuran, isopropyl ether, acetone, methyl ethyl ketone, methylene chloride or a mixture of these solvents.

Purified water is the solvent preferably used if the coating is devoid of effervescent agents; on the other hand, an organic solvent has to be used when the sprayed composition contains an effervescent acid/base pair.

An important advantage of the method of the invention is that it is very safe since it avoids the handling of fentanyl in the form of pulverulent mixtures, as is the case in the granulation and/or compression steps, and allows fentanyl to be contained by using the active substance in the form of a sprayed solution or suspension.

Fentanyl tablets according to the invention are useful in the management of breakthrough pain, in particular breakthrough cancer pain, by sublingual administration in patients who are tolerant to opioid therapy. Breakthrough pain means a transitory flare of pain of moderate to severe intensity occurring on a background of otherwise controlled pain.

It appears that the tablets according to the invention allow a rapid release of the fentanyl which is well absorbed by the sublingual mucosa.

The invention also relates to a method of treating pain which comprises introducing into the buccal cavity of a patient a therapeutically effective amount of a sublingual coated tablet of the invention. The term "patient" is understood to mean humans and other warm-blooded animals.

The method of treating pain according to the present invention is useful in the management of breakthrough pain, in particular breakthrough cancer pain. It is particularly suitable for treating patients who are already receiving and who are tolerant to opioid therapy for their underlying persistent pain.

Patients considered opioid tolerant are those who are taking at least 60 mg morphine/day, at least 25 µg transdermal fentanyl/hour, at least 30 mg of oxycodone daily, at least 8 mg of oral hydromorphone daily or an equianalgesic dose of another opioid for a week or longer.

The invention also relates to the use of fentanyl for the manufacture of a sublingual coated tablet according to the invention.

The so obtained sublingual coated tablets are particularly useful for treating breakthrough pain, in particular breakthrough cancer pain. It is particularly suitable for treating patients who are already receiving and who are tolerant to opioid therapy for their underlying persistent pain.

The invention will be understood more clearly from the following examples, without the latter in any way limiting the scope of said invention.

EXAMPLES

In the following examples, the below-mentioned products are used:

Granulated mannitol available under the trademark Parteck M300

Microcrystalline cellulose available under the trademark Avicel® PH200

Dihydrate dibasic calcium phosphate available under the name Emcompress

The given percentages are expressed by weight.

Example 1

1

Preparation of the Compressed Cores

Formula of the mixture of excipients
Parteck M300 (granulated mannitol): 49.75%
Avicel® PH200 (microcrystalline cellulose): 49.75%
Magnesium stearate: 0.50%

The excipients are mixed and compressed on a rotary tablet press.

The compressed cores have the following characteristics:
shape and size: round, flat chamfered tablets 6 mm in diameter.
mass 70 mg,
hardness: 150 N, as measured according to the method of the European Pharmacopeia $5^{th}$ Ed. (2.9.8)

2

Coating of the Compressed Cores

Formula of the coating solution
fentanyl citrate: 6.3 g
Opadry white 85F28751 (containing approximately 60% of HPMC calculated relative to the dry mass): 10.6 g
water: 300 g The coating solution is sprayed, in a perforated drum, onto 700 g of compressed cores, this mass corresponding to approximately 10 000 tablets.

The coated tablets obtained have a unit dosage of 0.63 mg of fentanyl citrate, i.e. 0.4 mg of fentanyl base.

Example 2

1

Preparation of the Compressed Cores

The excipients, in the amounts indicated in Table 1, are used to prepare the compressed cores.

TABLE 1

| Material | Batch Formula (g) | Unit Formula (mg/tablet) |
|---|---|---|
| Emcompress | 1200.0 | 56.0 |
| Avicel PH200 | 292.5 | 13.7 |
| Magnesium Stearate | 7.5 | 0.3 |
| Total | 1500.0 | 70.0 |

A pre-mix of Emcompress and Avicel was prepared by mixing in a cube mixer during 10 min at 40 rpm. Said pre-mix was lubricated by mixing with magnesium stearate in a cubic mixer during 1 min at 40 rpm.

Compression is performed using a tabletting machine PR12 equipped punches of diameter 5.5 mm.

The compressed cores have a round biconvex shape

Characteristics of compressed cores are given in Table 2.

TABLE 2

| average hardness (N) | 41.8 N |
|---|---|
| thickness (mm) | 1.55 mm |
| average tableting force (kg) | 2000 kg |

Spraying of Fentanyl and Then of Alkaline Agent Onto the Compressed Cores

The formula of coating tablets is given in Table 3.

The suspension in water of fentanyl citrate and Opadry II yellow is sprayed on the compressed cores obtained in the previous step in a drilled pan Trislot. In a second step, disodium phosphate together with PEG6000 is sprayed on the just obtained coated fentanyl tablets using the same equipment as for the application of fentanyl citrate and Opadry in the previous step.

TABLE 3

| Material | Batch Formula (g) | % Formula |
|---|---|---|
| Compressed cores | 1003.00 | 94.41 |
| Fentanyl citrate | 9.00 | 0.85 |
| Opadry II Yellow | 21.56 | 2.03 |
| Anhydrous disodium phosphate | 14.37 | 1.35 |
| PEG 6000 | 14.40 | 1.36 |
| Purified water | 718.00 | — |
| Total dry weight | 1062.33 | 100.0 |

Tablets obtained presented the characteristics are given in Tables 4 and Table 5.

TABLE 4

| Colour | Deep beige |
|---|---|
| Form | Round biconvex |
| Diameter | 5.6 mm |
| Thickness | 1.8 mm |
| Theoretical dry weight | 1062.3 g |
| Theoretical fentanyl content | 0.40 mg/g |
| Weight yield | 100.1% |

TABLE 5

| Determination | Methods | Specifications | Results |
|---|---|---|---|
| Fentanyl content (expressed as base) | HPLC | 0.40 mg/tablet ± 10% (0.36-0.44 mg/tablet) | 0.38 mg/tablet |

Example 3

A Crossover Single-Dose Comparative Bioavailability Study of Tablets prepared according to example 2 versus Actiq® 0.4 mg was performed in Healthy Male Volunteers under Fasting Conditions The objective of this pilot study was to assess the single-dose relative bioavailability of both formulations in healthy male volunteers under fasting conditions.

Tablets prepared according to example 2 and the reference product which were each administered to 10 patients and the Cmax, Tmax and AUC were measured.

The reference product is a fentanyl citrate formulation (solid drug matrix on a handle) designed to facilitate transmucosal absorption and marketed worldwide under trademark Actiq®.

Both the invention and the reference product contain fentanyl citrate in an amount equivalent to 0.4 mg of fentanyl base.

Blood sampling points: before dosing and at the following times thereafter in each period: 5, 10, 15, 20, 25, 30, 35, 40, 45, 50, 60, 75, 90 minutes and at 2, 3, 4, 6, 8, 12 and 24 hours post-dose The AUC 0-t, $AUC_\infty$, Cmax, tmax pharmacokinetic parameters were calculated for fentanyl in plasma.

Geometric means are given in Table 6:

TABLE 6

| Parameter(CV %) | Invention (n = 10) | Actiq ® 0.4 mg(n = 10) |
|---|---|---|
| AUC 0-t (pg · h/mL) | 4587.52 (24.6%) | 3059.25 (33.1%) |
| $AUC_{oc}$ (pg · h/mL) | 5204.72 (30.2%) | 3473.98 (37.0%) |
| Cmax (pg/mL) | 678.895 (28.1%) | 406.614 (27.1%) |
| tmax* (h) | 1.5 [0.4-3.00] | 2.0 [1.0-3.0] |

*median [range]

Mean Ratios of the invention versus Actiq® are calculated in table 7 below

| Parameter | Invention vs. Astiq ® |
|---|---|
| AUC 0-t | 146.4% |
| $AUC_{oc}$ | 146.2% |
| Cmax | 160.4% |
| tmax (h)* | −0.75 |

*Median difference (test − reference).

The results are also presented in FIG. 1.

The fentanyl formulation according to invention displays improved pharmacokinetics with an earlier tmax and highly enhances bioavailability in comparison to the reference product (Actiq®).

The invention claimed is:

1. A sublingual coated tablet comprising
a compressed core devoid of pharmaceutically active substance and comprising one or more diluting agents, and
a sprayed coating comprising at least fentanyl as active substance and applied onto the compressed core from a solution, a suspension or a colloidal dispersion of fentanyl,
wherein said one or more diluting agents comprises dicalcium phosphate which represents between 50 and 95% by mass of the compressed core.

2. The sublingual coated tablet according to claim 1, wherein the compressed core also comprises one or more excipients selected from the group comprising binders, swelling agents, disintegrating agents, lubricants, antistatic agents and adjuvants, and mixtures thereof.

3. The sublingual coated tablet according to claim 1, wherein the sprayed coating comprises at least one excipient.

4. The sublingual coated tablet according to claim 3, wherein the excipient is selected from the group comprising binders, soluble agents, surfactants, absorption promoters, antistatic agents, pH modifiers, acid/base pairs that produce an effervescence, sweeteners, flavourings and dyes, and mixtures thereof.

5. The sublingual coated tablet according to claim 1, wherein fentanyl as active substance is selected from the group comprising fentanyl, fentanyl citrate, fentanyl hydrochloride, alfentanil, alfentanil hydrochloride, sufentanil, sufentanil citrate, remifentanil, remifentanil hydrochloride, in the form of their pharmaceutically acceptable salts, in any polymorphic form, in racemic or enantiomeric form.

6. The sublingual coated tablet according to claim 1 which further comprises a coating containing an alkaline compound selected from the group comprising tris, tartrate, acetate, phosphate, and mixtures thereof.

7. A method for preparing a sublingual coated tablet according to claim 1, comprising the following steps:
   a. providing a compressed core devoid of pharmaceutically active substance and comprising one or more diluting agents;
   b. spraying said compressed core with a coating comprising at least fentanyl as active substance, wherein the coating is applied onto the compressed core from a solution, a suspension or a colloidal dispersion of fentanyl, wherein said one or more diluting agents comprises dicalcium phosphate which represents between 50 and 95% by mass of the compressed core.

8. The method according to claim 7, comprising a step of spraying a solution or suspension comprising an alkaline compound and, optionally, at least one pharmaceutically acceptable excipient, said step being carried out before, after or simultaneously with step b.

9. The method according to claim 7, wherein the solution or the suspension comprising fentanyl comprises at least one excipient.

10. The method according to claim 8, wherein the solution or the suspension comprising the alkaline compound comprises at least one excipient.

11. The method according to claim 9, wherein the solution or the suspension comprising fentanyl is an aqueous solution or suspension.

12. The method according to claim 10, wherein the solution or the suspension comprising the alkaline compound is an aqueous solution or suspension.

13. A method of treating pain which comprises introducing into the oral cavity of a patient a therapeutically effective amount of a sublingual coated tablet according to claim 1.

14. The method according to claim 13, in which the pain is breakthrough pain.

15. The method according to claim 14, in which the breakthrough pain is breakthrough cancer pain.

16. The method according to claim 13, in which the patient is already under opioid therapy.

17. The sublingual coated tablet according to claim 1 wherein the compressed core comprises dicalcium phosphate, microcrystalline cellulose and a lubricant.

18. The sublingual coated tablet according to claim 4, wherein the binder is selected from polyvinylpyrrolidones, cellulose-based polymers, acrylic polymers and polyethylene glycols.

19. The sublingual coated tablet according to claim 18, wherein the cellulose-based polymer is hydroxypropylmethylcellulose.

20. The sublingual coated tablet according to claim 6, wherein the coating containing the alkaline agent further comprises polyethylene glycol.

21. The sublingual coated tablet according to claim 1, having a disintegration time greater than 1 minute and less than 15 minutes.

22. The sublingual coated tablet according to claim 1, wherein said sprayed coating comprising fentanyl is coated with a layer comprising an alkaline compound.

23. The sublingual coated tablet according to claim 1 which further comprises a coating containing anhydrous disodium phosphate.

* * * * *